United States Patent [19]

Buonaiuto et al.

[11] Patent Number: 5,651,940
[45] Date of Patent: Jul. 29, 1997

[54] SEALED SAMPLE CUVETTE FOR VOLATILE SOLUTIONS

[75] Inventors: Val Buonaiuto, Mountain View; Taro Nogami, San Jose, both of Calif.

[73] Assignee: Hitachi Instruments, Inc., San Jose, Calif.

[21] Appl. No.: 578,452

[22] Filed: Dec. 26, 1995

[51] Int. Cl.$^6$ .................................................. B01L 3/00
[52] U.S. Cl. .................. 422/102; 422/103; 220/203.21; 220/281; 220/361; 215/312
[58] Field of Search .................. 220/203.21, 281, 220/361; 215/247, 312; 422/102, 103

[56] References Cited

U.S. PATENT DOCUMENTS

| | | | |
|---|---|---|---|
| 811,811 | 2/1906 | Allison | 215/247 |
| 1,416,278 | 5/1922 | Furman . | |
| 2,059,685 | 11/1936 | Feldman | 215/312 |
| 3,635,092 | 1/1972 | Maughan et al. | 73/421.5 R |
| 3,750,822 | 8/1973 | Dubach | 215/52 |
| 3,886,800 | 6/1975 | Boehringer | 73/421.5 R |
| 4,056,120 | 11/1977 | MacNeilage | 220/203.21 |
| 4,134,512 | 1/1979 | Nugent | 215/247 |
| 4,515,752 | 5/1985 | Miramanda | 422/99 |
| 4,736,083 | 4/1988 | Saville | 215/312 |
| 4,812,293 | 3/1989 | McLaurin et al. | 422/69 |
| 4,954,149 | 9/1990 | Fullemann | 55/386 |
| 5,368,177 | 11/1994 | Derksen | 215/249 |
| 5,413,230 | 5/1995 | Folter et al. | 220/281 |

FOREIGN PATENT DOCUMENTS

| | | | |
|---|---|---|---|
| 181834 | 3/1907 | Germany | 215/312 |
| 436259 | 12/1925 | Germany | 215/312 |

Primary Examiner—Jeffrey Snay
Attorney, Agent, or Firm—John J. Sideris

[57] ABSTRACT

The sealing apparatus of the present invention is a sample cuvette cap having a hole for inserting the nozzle of an auto-sampler therethrough. Located within the lumen of the hole is a small detent ball that can be positioned to block the lumen. The detent ball, which can be spring-operated or gravity-operated, blocks the fluid flow in the hole in its normal, closed position. When the auto-sampler nozzle hits the ball, the ball becomes deflected to one side into a recess, due to a difference in the nozzle axis relative to the center of the ball. By the dislocating the detent ball, the nozzle can be inserted into the cuvette smoothly as the air goes in and out through the space around the nozzle. This allows the pressure in the cuvette to be kept constant. After the nozzle is removed, the ball returns to its original position by gravity or by the force of a spring, resealing the cuvette. All of the parts for the sealing apparatus are solid parts which can be easily cleaned and reused. Because there is no non-recoverable distortion or damage to the sealing mechanism, it can be re-used after cleaning.

14 Claims, 6 Drawing Sheets

SEALED SAMPLE CUVETTE FOR VOLATILE SOLUTIONS

FIELD OF THE INVENTION

The present invention relates generally to the accurate measurement and analysis of samples in an analytical system, and in particular to a sealed cuvette apparatus and method for reducing concentration errors induced during the sampling step of a quantitative analysis process.

BACKGROUND OF THE INVENTION

Auto-samplers are used for routine analyses in many types of analytical systems such a liquid chromatography systems, gas chromatography systems, spectrophotometry systems and the like. Generally, the number of samples installed in a typical auto-sampler rack is increasing as the technology becomes more affordable. In most auto-samplers, the samples themselves are dissolved in volatile solvents, which tend to evaporate over time. In order to minimize concentration errors caused by such evaporation, it is necessary to seal the sample cuvettes while the samples are in the rack awaiting analysis. Reducing concentration errors is especially important in quantitative analysis.

The conventional method for sealing a cuvette is to use a flexible septum for sealing the top of the cuvette. The septum is then punctured by the nozzle of the auto-sampler during the sampling step. However, the flexible septum has two major problems. First, there are pressure changes produced in the cuvette when the nozzle presses the flexible septum into the cuvette during the puncture. There are also pressure changes produced when the nozzle aspirates the sample solution, and when the nozzle is retracted from the cuvette. These pressure changes are induced because the flexible septum material tightly contacts the nozzle during its movement, blocking air flow.

Figure 1:
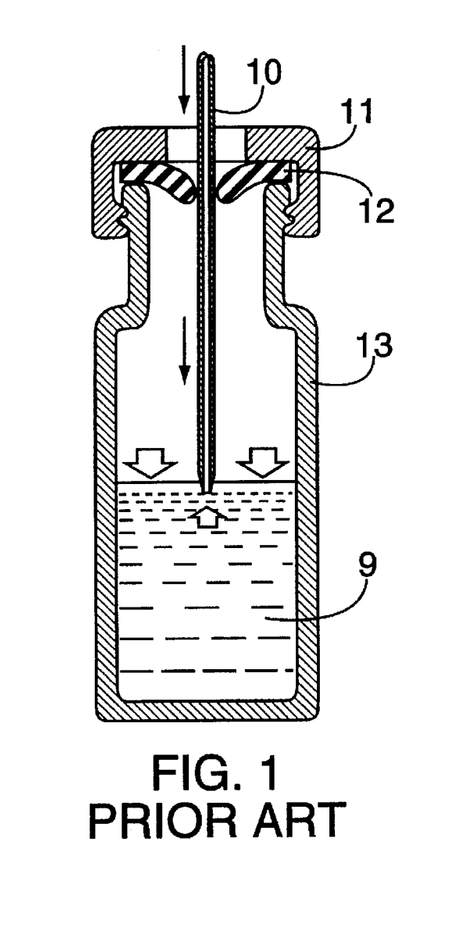
FIG. 1, FIG. 2 and FIG. 3 show the pressure changes occurring when prior art sealed sample cuvettes are used.
Figure 2:
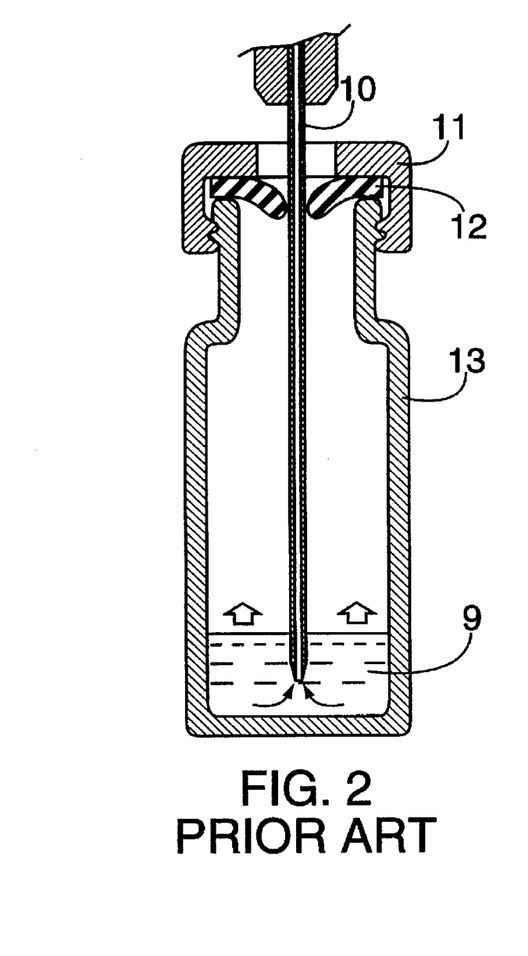
Figure 3:
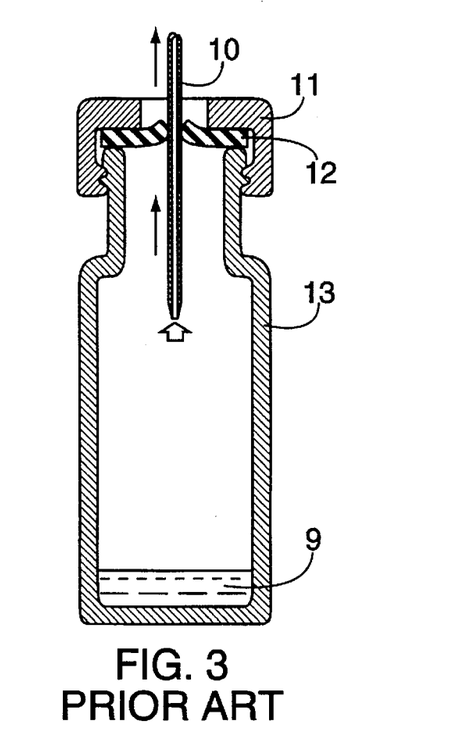

FIG. 1, FIG. 2 and FIG. 3 show the problem of pressure changes for the conventional sealed cuvette. FIG. 1 shows the pressure change when the nozzle is inserted. A conventional septum 12 is secured over the opening of a cuvette 13 by a cap 11. The cuvette container 13 holds the sample in it. The internal capacity of the cuvette 13 decreases when the nozzle 10 hits the septum 12 and pushes it down. The capacity of the cuvette 13 continues decreasing as the nozzle 10 continues its downward travel through the septum 12. As can be understood, the pressure in the cuvette increases. This may cause a small amount of air or sample to be pushed into the nozzle 10 in some instances. If the pressure changes are large, there is the possibility of bubbles forming in the sample solution, replacing sample with air in the nozzle 10.

FIG. 2 shows the pressure change during aspiration of the sample. During aspiration of the sample, the pressure in the cuvette 13 tends to decrease, causing an insufficient aspiration. In some cases, air may leak through the torn septum 12 and correct the pressure decrease. But this does not always occur, especially if the septum is flexible enough to make an air-tight contact with the nozzle 10.

FIG. 3 shows the pressure change when the nozzle 10 is removed. The pressure tends to decrease because of the shape change of the septum 12 and also the volume decrease of the nozzle 10 located inside of the cuvette 13. Usually, the sample held in the nozzle 10 is located between two air bands. The band of sample can be pulled down slightly by the pressure decrease. This inconsistency causes bad reproducibility of the analytical data.

In general, these pressure changes often produce excess or insufficient sample aspiration, and cause quantitative errors. If enough sample volume is available, a cut volume injection mode (which discards both ends of the aspirated sample and picks up only the middle portion) can be used. This technique minimizes the quantitative errors caused by excess or insufficient aspiration. However, there is the possibility that an incorrect amount of sample will be injected into the analytical system if the sample position in the nozzle is disturbed by a pressure change, such as during removal of the nozzle.

In many cases, a total volume injection mode must be used (all of the sample is picked up), especially when the available sample volume is small. In such a case, the excess or insufficient sample aspiration during total volume injection causes problems. The pressure change caused by the nozzle movement or the sample aspiration disturbs the nozzle's ability to hold the exact amount of sample at the exact position in the nozzle, resulting in quantitative errors. These errors frequently occur when total volume injection mode is used for small volume samples.

Figure 4:
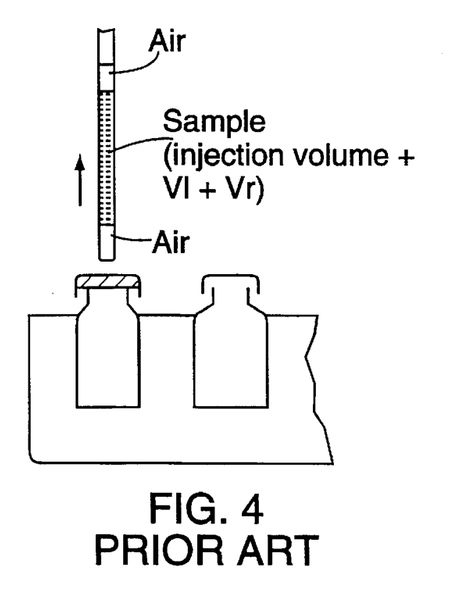
FIG. 4 and FIG. 5 show the difference between cut volume injection and total volume injection modes used during the sampling step of an analysis.
Figure 5:
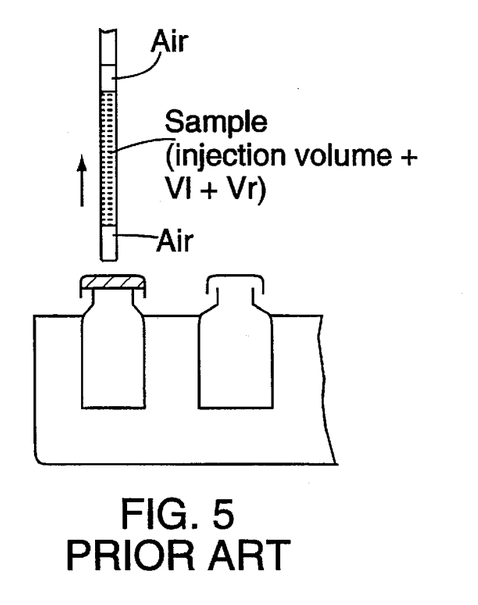

FIG. 4 and FIG. 5 show the difference between the cut volume injection mode and the total volume injection mode. FIG. 4 is a diagram of the cut volume injection mode. Since enough sample volume is available, the auto-sampler aspirates more volume than the volume necessary for analysis. The auto-sampler aspirates leading volume vl plus injection rear volume vr. After the aspiration, the auto-sampler pushes out vr into a drain (not shown), injects the injection volume of the sample into the analytical system and pushes out the rest of the sample, vl, into the drain. Whenever the aspiration volume or the location of a sample in the nozzle 10 is disturbed by a pressure change in the cuvette, vl or vr is affected. The volume which is actually injected into the analytical system is not affected as much.

FIG. 5 is a diagram for the total injection mode. This mode must be used if enough sample volume for the cut volume mode is not available. The auto-sampler aspirates the same volume as the volume which must be injected into the analytical system. The air layers at both ends of the sample in the nozzle 10 are for holding the sample. The top-side air layer is pushed out before injection of the sample, and the auto-sampler stops injecting before the other side air layer reaches the tip of the nozzle 10. However, this control cannot be implemented correctly if the amount of aspirated sample or the location of it is not precise. The incorrect and inconsistent volume of sample aspiration causes erroneous and inconsistent quantitative data, since the aspirated volume is directly injected into the analytical system. In addition, the incorrect position of the sample in the nozzle 10 can also cause incorrect quantitative data results.

The second major problem that arises in conventional flexible septum sealers comes from the fact that none of the current sealing septa are reusable since they cannot reseal the cuvette after being punctured. As mentioned above, this leads to evaporation of the sample solution, causing concentration errors.

To overcome the problems of induced pressure changes, a prescored septum or a septum made of non-flexible material is sometimes used. These septa are punctured by the nozzle before aspiration of the sample solution. Air is allowed to pass into and out of the cuvette, thereby maintaining a constant atmospheric pressure level.

Figure 6A:
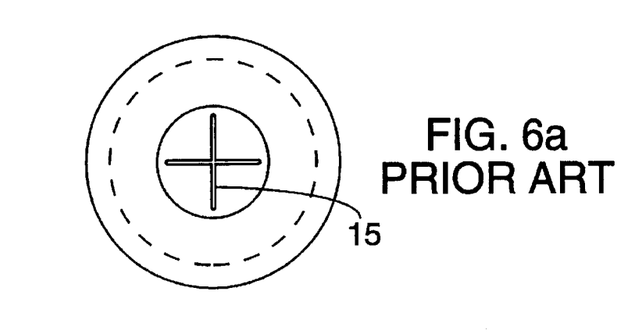
FIGS. 6(a) & (b) and FIG. 7 show prior art devices for reducing the problem caused by pressure changes induced during the sampling step of an analysis.
Figure 6B:
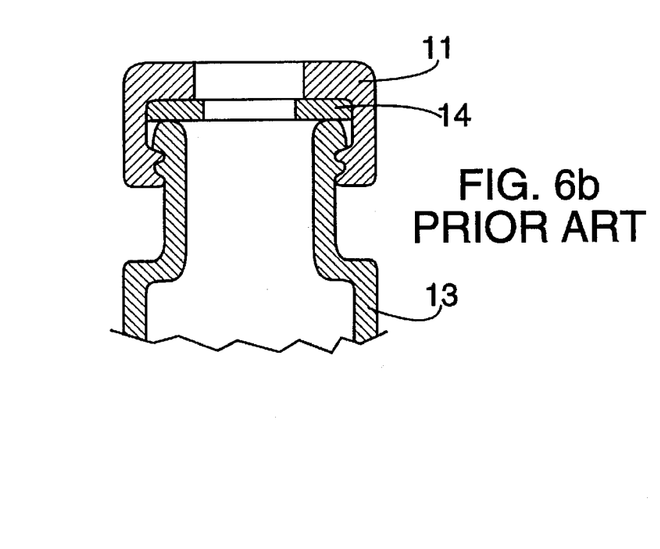

FIG. 6 (a) is a top view and (b) is a cross-sectional side view of a pre-scored septum 14. The sealed cuvette contains essentially the same parts as the parts shown in FIG. 1, FIG. 2 and FIG. 3, except for the different septum 14. The pre-scored septum 14 has a cross score 15. When the septum 14 is punctured, the score 15 is expanded slightly for air flow along the inserted nozzle (not shown), and pressure changes can be avoided. However, this prior art technique results in an imperfect sealing of the cuvette. There is a small leakage of air even before the septum 14 is punctured. These septa cannot completely seal the cuvettes while sitting in the auto-sampler racks awaiting analysis, thereby exposing the sample to possible undesirable evaporation/concentration errors.

When, instead, using the septum made of a non-flexible material, problems occur from minute particle containments of the septum material that are easily produced from the scratching and friction that occurs between the septum material and the nozzle edge during contact. In addition, these non-flexible septa are not reusable and must be discarded after being punctured.

Figure 7:
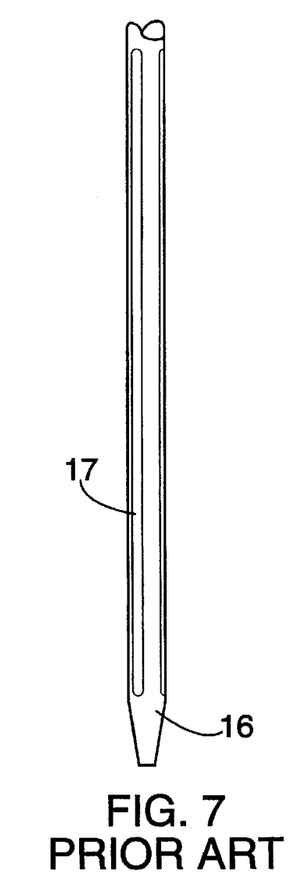

Another method currently practiced to reduce the problem caused by pressure changes associated with a flexible septum is to use a special auto-sampler nozzle which contains longitudinal grooves along its exterior surface. Air is allowed to pass into and out of the cuvette through the spaces created between the grooves and the septum. FIG. 7 shows a schematic view of a grooved nozzle 16. As the grooved nozzle 16 penetrates the septum, air flows along the spaces in the grooves 17, avoiding any large pressure changes in the cuvette. However, cam must be taken in choosing the material of the septum. Some septa are too flexible, and may block the air flow through the grooves 17. In addition, consideration must be given as to properly washing the grooved nozzle 16 in order to prevent carry over contamination from other samples.

Thus, there is a need for a cuvette septum which does not introduce contaminants to the sample or pressure changes during the insertion and removal of an auto-sampler nozzle, and which is resealable so as to prevent the evaporation of the sample solvent.

Accordingly, it is an object of the present invention to provide a sealer for a sample cuvette which can be penetrated by an auto-sampler nozzle without producing errors caused by pressure changes induced in the cuvette.

It is another object of the present invention to provide a sealer for a sample cuvette that permits the precise aspiration of the sample solution contained therein.

It is a further object of the present invention to provide a sealer for a sample cuvette that can provide a tight seal for the cuvette before insertion by a nozzle and that can reseal the cuvette after the nozzle is removed.

It is another object of the present invention to provide a sealer for a sample cuvette that can avoid the carry over contamination problems that may affect the accurate analysis of the sample.

It is another object of the present invention to accomplish the above-stated objects by utilizing an apparatus which is simple in design and use, and economical to manufacture.

The foregoing objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel methods, arrangements, combinations and improvements herein shown and described.

SUMMARY OF THE INVENTION

In accordance with these and other objects of the invention, a brief summary of the present invention is presented. Some simplifications and omissions may be made in the following summary, which is intended to highlight and introduce some aspects of the present invention, but not to limit its scope. Detailed descriptions of preferred exemplary embodiments adequate to allow those of ordinary skill in the art to make and use the inventive concepts will follow in later sections.

According to a broad aspect of the invention, an apparatus and method for sealing a sample cuvette is disclosed. The apparatus is a resealable cap for a container for permitting the sampling of a fluid by extension of the nozzle of a probe therethrough. The cap has an annular bore defining a lumen having a proximal end and a distal end. The lumen includes a depression along its inner surface between the proximal and distal ends. The cap includes a chamber in fluid communication with the lumen positioned opposite the depression, and a movable sealing element located in the chamber and dimensioned to conform with the depression. The sealing element can be urged into sealing engagement with the depression to block the flow of fluid through the lumen, or the sealing element can be deflected into the chamber to permit access of the nozzle with the interior of the container. The cap further includes a spring element positioned in the chamber to bias the sealing element in a sealing engagement with the depression and a removable stopper positioned in the chamber to retain the sealing element therein and to allow removal of the sealing element for maintenance purposes. The sealing element is preferably a detent ball. In another embodiment, the chamber connects to the lumen at an acute angle such that the direction of the force of gravity is closer to the direction of the movement of the sealing element, requiring less force to move the sealing element against the force of the spring.

Also disclosed is a method of accessing a container through a resealable cap while maintaining a constant pressure in the container; the cap having a bore therethrough, a chamber in communication with the bore and a sealing member disposed in the bore that blocks fluid flow through the bore in a normal position and that allows access of a probe in another position. The method includes the steps of inserting a probe through the bore into contact with the sealing member; displacing the sealing member out of the bore and into the chamber as the probe moves past the sealing member; and returning the sealing member into the normal position blocking fluid flow through the bore after the probe is withdrawn.

DETAILED DESCRIPTION OF PREFERRED EMBODIMENTS OF THE INVENTION

The present invention is directed to solving the problem of quantitative errors caused by evaporation and by pressure changes in a sealed cuvette for an auto-sampler influenced by movements of the nozzle of the auto-sampler and the aspiration of the sample in the cuvette. It is to be understood that the present invention may be used with equal facility and advantage with various containers or vessels, and that the following description of a sample cuvette, related to but not forming part of the invention, is provided for illustrative purposes only.

Figure 8:
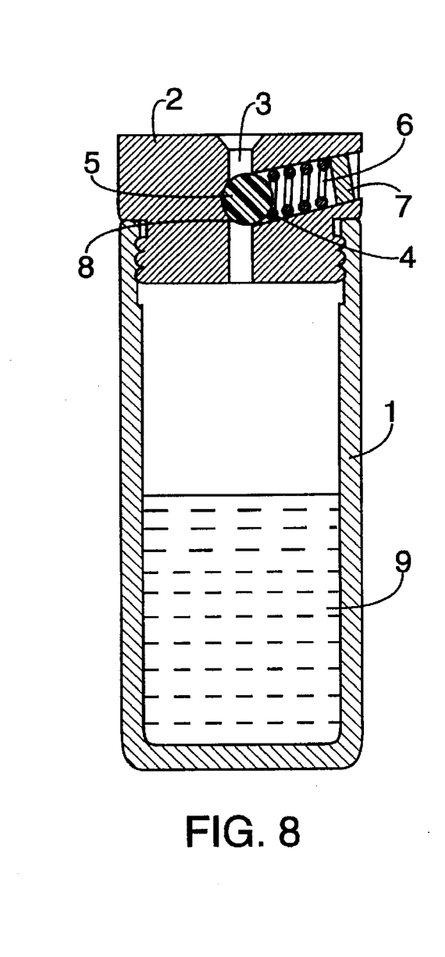
FIG. 8 is a schematic view showing a cross-section of a sealed sample cuvette according to one embodiment of the present invention.

Referring now to the drawings, wherein like numerals refer to like components, there is disclosed in FIG. 8 a general arrangement of a sealed cuvette according to one embodiment of the present invention. The sealed cuvette comprises a cuvette body 1, typically made of glass and a cap 2, preferably threaded, which has a longitudinal hole (or bore) defining a lumen 3 approximately at its center. Cap 2 is made of a resilient or solid material. Preferably, the proximal end of lumen 3 is tapered to facilitate insertion of a nozzle therein.

The cap 2 includes a compartment or chamber 4 which is in communication with the lumen 3 and angled upward therefrom, and a sealing member or element 5 disposed in the lumen 3 and dimensioned to fit within compartment 4. In the preferred embodiment of the present invention, the sealing element is a detent ball 5 of the type common in the industry.

It should be noted that although the detent ball 5 described herein is the type commonly encountered by those skilled in the art, the invention is not so limited. The particular sealing element 5 used for the purpose of blocking lumen 3 is not limited to a spherical ball. Accordingly, other shaped elements known in the art, such as a bevel edged shaft or a shaft having a tapered edge facing the nozzle 10 (similar to the locking bolt of a self closing lock) may be used to accomplish a similar result and still be within the scope of the invention.

The cap further includes a spring mechanism 6 located in compartment 4 which biases the ball 5 into a sealing engagement with the lumen 3, and a stopper 7 located at one end of compartment 4 for retaining ball 5 and spring 6 therein. The lumen 3 includes a recessed area or depression 8 along its inner surface. Recess 8 is dimensioned and positioned to receive the ball 5 urged therein by spring 6. Stopper 7 is removably secured to cap 2 to permit removal of spring 6 and ball 5 for cleaning and maintaining the cap 2 and all components contained therein. The stopper 7 may be secured by a frictional force fit, or preferably by a threaded engagement (threads not shown for clarity).

When the sealed cuvette is 1 used for sample analysis, it is filled with a sample solution 9.

Figure 9:
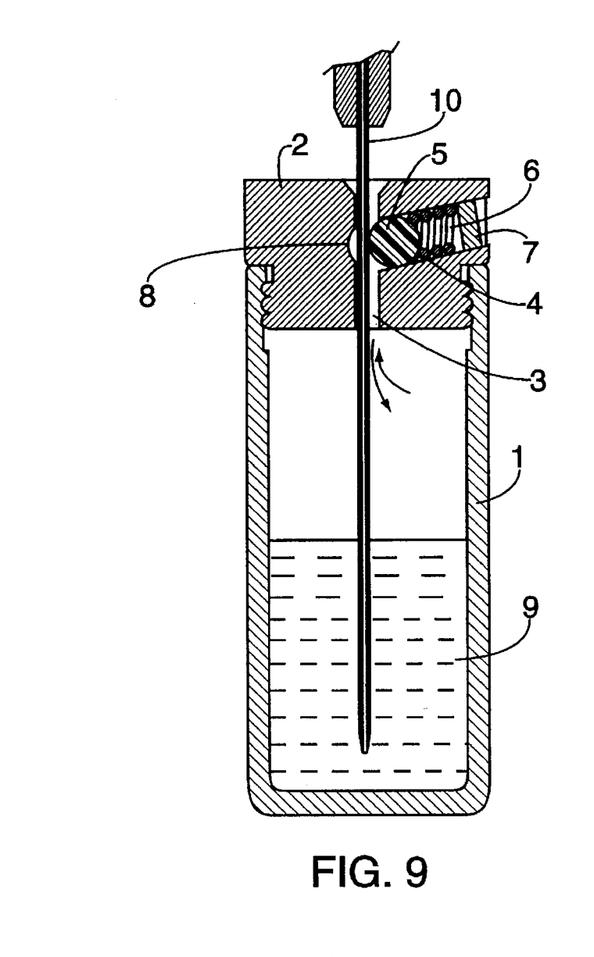
FIG. 9 is a schematic view showing a cross-section of a sealed sample cuvette of FIG. 8 during insertion of an auto-sampler nozzle, according to one embodiment of the present invention.

FIG. 9 shows a cross-section of the sealed sample cuvette 1 of FIG. 8 during insertion of a probe, such as a needle. In our case, the probe is an auto-sampler nozzle 10. Nozzle 10 is inserted into lumen 3 of cap 2. Before the nozzle 10 deflects the balls into compartment 4, the ball 5 is positioned under the force of spring 6 such that its center is closer to the compartment 4 than the center position of the vertical axis of lumen 3 (or nozzle 10). Thus, when the nozzle 10 contacts the ball 5 (off of its center axis), the ball 5 is easily deflected aside into the compartment 4.

Due to the spherical shape of the ball 5, no sliding seal occurs around the nozzle 10, and there is room for air to flow along the nozzle 10 to prevent pressure changes in the cuvette 1 during sample aspiration and nozzle 10 insertion/removal. The pressure in the cuvette 1 will be the same as the atmospheric pressure even when the nozzle 10 moves up or down in the cuvette 1 or when the sample solution 9 is aspirated. This pressure stabilization in the cuvette 1 prevents excess aspiration, insufficient aspiration and dislocation of the aspirated sample 9 in the nozzle 10. It also reduces the possibility of the many types of error caused by bubbles produced by pressure changes.

The sample solution 9 is usually a volatile liquid which undergoes evaporation over time. However, because ball 5 is urged into recess 8 by spring 6 to form a seal, evaporation through lumen 3 is prevented. The force of spring 6 is set to provide rapid closure as the nozzle 10 is removed and to provide reliable sealing of the cap 2. This seal is well suited for both automatic and manual insertion of nozzle 10.

Figure 10:
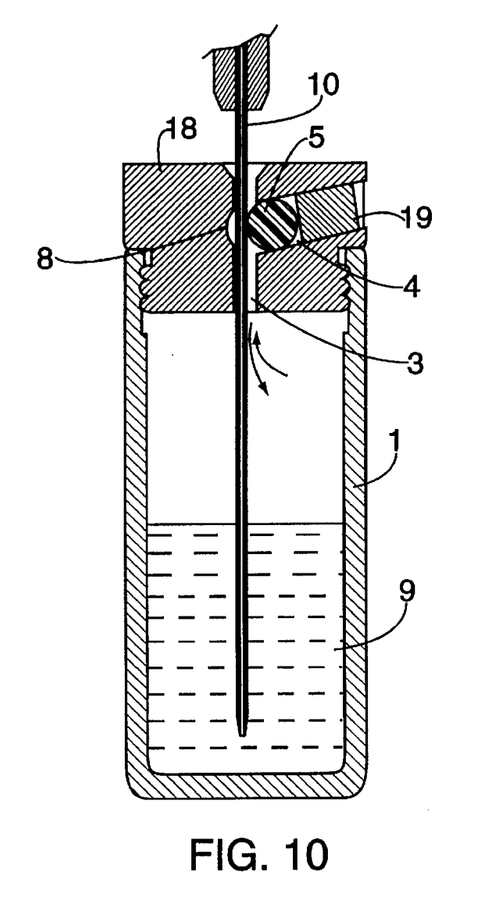
FIG. 10 is a schematic view showing a cross-section of a sealed sample cuvette according to another embodiment of the present invention.

Turning now to FIG. 10, a schematic view showing a cross-section of a sealed sample cuvette 1 according to another embodiment of the present invention is disclosed. In this embodiment, the threaded cap 18 does not include a spring which presses the ball 5 into the position for closing the lumen 3. Instead, the ball 5 is gravity operated. Under the force of gravity, the ball 5 is urged into recess 8 to form a seal. As the nozzle 10 is inserted, the ball 5 is deflected into compartment 4. The cap 2 includes removable stopper 19 for limiting the range of movement of ball 5 within compartment 4.

Figure 11:
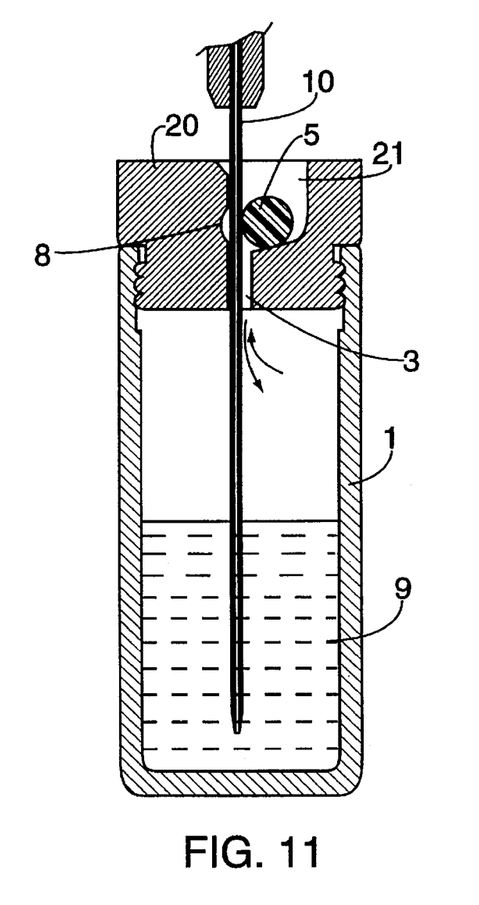
FIG. 11 is a schematic view showing a cross-section of a sealed sample cuvette according to yet another embodiment of the present invention.

FIG. 11 is a schematic view of yet another embodiment of the present invention. As in the embodiment shown in FIG. 10, the ball 5 is urged into the position in recess 8 for closing the lumen 3 by the force of gravity. The threaded cap 20 includes an arcuate-shaped compartment 4 that is accessible at its proximal end. At the distal end of compartment 4, when the nozzle 10 is not present in lumen 3, the ball 5 rests against recess 8, blocking lumen 3 and thereby forming a seal. When the nozzle 10 is inserted through lumen 3, ball 5 is deflected upward and further into compartment 4. Advantageously, the proximal end of compartment 4 allows for easy access to ball 5 and compartment 4 for cleaning and maintenance thereof. In addition, compartment 4 provides for increased air flow for faster pressure stabilization of the cuvette 1 during sample aspiration and insertion or removal of nozzle 10.

Figure 12:
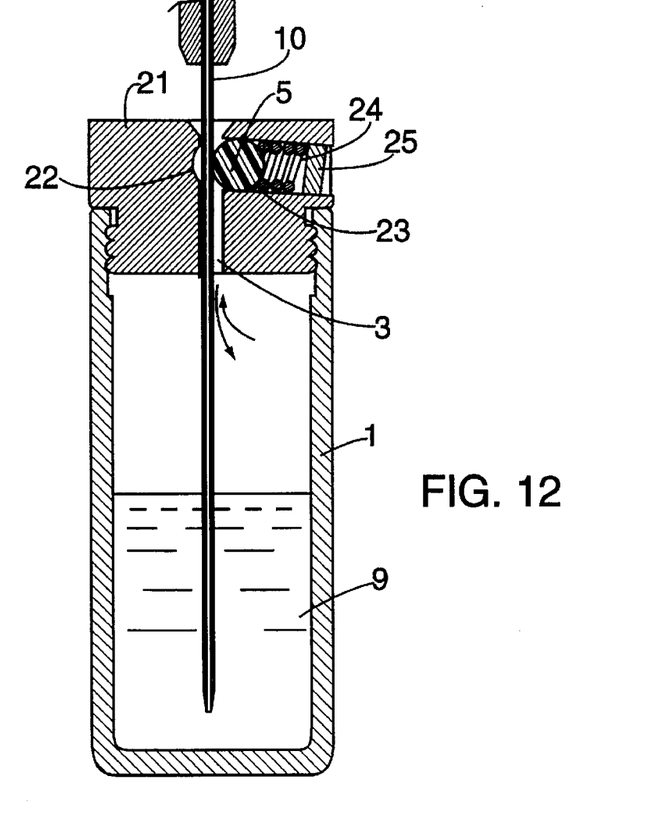
FIG. 12 is a schematic view showing a cross-section of a sealed sample cuvette according to yet another embodiment of the present invention.

FIG. 12 is a schematic view of still another embodiment of the present invention. As seen in FIG. 12, one difference between the embodiment of FIGS. 8 and 9 and the embodiment of FIG. 12 is that the latter has a compartment 23 acutely angled, away from lumen 3. A spring 24 urges the detent ball 5 up from the lower end of compartment 4 into a sealing engagement with recess 22, to block fluid flow through lumen 3. Stopper 25 retains spring 24 and ball 5 within compartment 4. When the ball 5 seals lumen 3, the top of the ball 5 closes the lumen 3. Advantageously, the direction of the force of the needle is closer to the direction of the movement of the ball 5 such that the ball 5 can be moved by the nozzle 10 by a smaller force than in the previously described embodiments, requiring less nozzle driving power.

Figure 13:
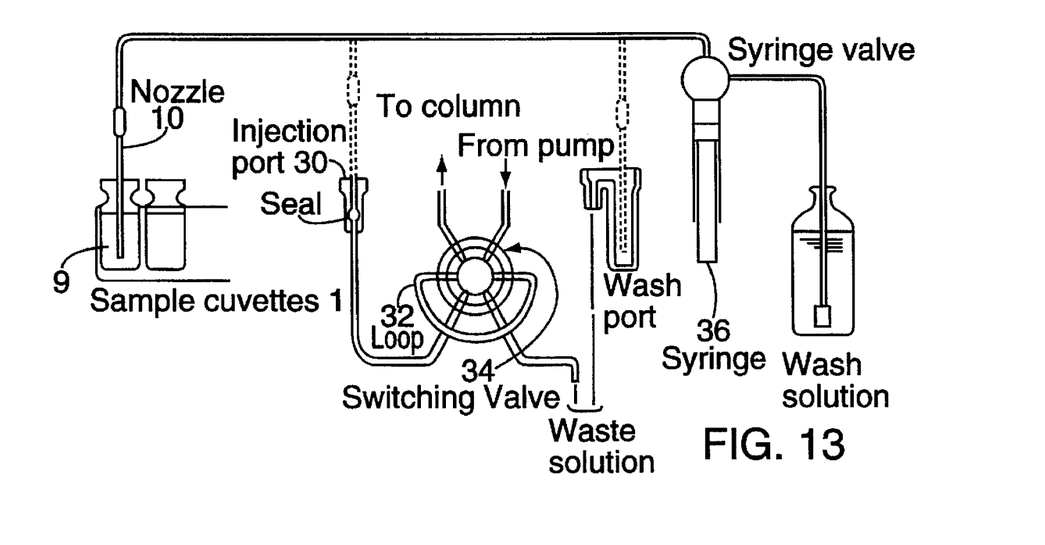
FIG. 13 is a flow diagram of an auto-sampler using a sealed sample cuvette of the present invention.

FIG. 13 shows a flow diagram of an auto-sampler of HPLC using sealed sample cuvettes 1 of the present invention. A nozzle 10 picks up sample 9 from a sealed sample cuvette 1 and injects it into an injection port 30 and pushes it towards a loop 32 of a switching valve 34. After the sample reaches the loop 32 of the switching valve 34, the switching valve 34 switches the flow paths so that a flow from a pump (not shown) can push the sample 9 towards a column (not shown). The aspiration of sample 9 from the cuvette 1 and the injection of sample 9 into the loop 32 via the injection port 30 are driven by movements of a syringe 36. The samples may stay in the cuvettes 1 for a long time before being aspirated. The sealing mechanism of the present invention prevents evaporation of the sample solutions 9 in the cuvettes 1 during this waiting period.

As can be understood by those skilled in the art, the sealing mechanism of the present invention can be used with nozzles of various diameters, limited only by the diameter of lumen 3. Moreover, unlike the prior art septa, the present invention is reusable after insertion and removal of the nozzle 10 during the sampling step. Quantitative errors caused by evaporation of the sample solution are preventing due to the resealable feature of cap 2. Finally, all of the parts for the sealing apparatus are solid parts which can be easily cleaned and reused. Because there is no non-recoverable distortion or damage to the sealing apparatus, it can be m-used after cleaning.

Although the invention has been described in detail with particular reference to several preferred embodiments thereof, it should be understood that the invention is capable of other and different embodiments, and its details are capable of modifications in various obvious respects. As is readily apparent to those skilled in the art, variations and modifications can be affected while remaining within the spirit and scope of the invention. Accordingly, the foregoing disclosure, description, and FIGS. are for illustrative purposes only, and do not in any way limit the invention, which is defined only by the claims.

What is claimed is:

1. A resealable cap for a container for permitting the sampling of a fluid disposed in the container by extension of the nozzle of a probe through said cap, said cap comprising:

an annular bore having an axis and defining a straight lumen having a proximal end and a distal end, wherein said lumen includes a depression along its inner surface between said proximal and distal ends;

a chamber in fluid communication with said lumen and positioned alongside said depression, wherein said chamber has an axis disposed at an acute angle greater than zero degrees with respect to the axis of said annular bore; and a movable sealing element disposed in said annular bore and dimensioned to conform with said depression, wherein said sealing element can be urged into sealing engagement with said depression to block the flow of fluid through said lumen, or said sealing element can be deflected into said chamber to permit access of said nozzle with the interior of the container.

2. A resealable cap for a container according to claim 1, wherein said chamber is in communication with said lumen on one end and is a bore through said cap on another end; said cap further comprising a removable stopper disposed in said chamber to retain said sealing element therein.

3. A resealable cap for a container according to claim 1 wherein said container is a sample cuvette.

4. A resealable cap for a container according to claim 1, further comprising a spring mechanism disposed in said chamber to bias said sealing element in a sealing engagement with said depression.

5. A resealable cap for a container according to claim 4, wherein said chamber connects to said lumen at an acute angle greater than zero degrees such that the direction of the movement of said sealing element is partially in the direction of the force of the needle, thereby requiring less force to move said sealing element against the force of said spring.

6. A resealable cap for a container according to claim 1, wherein said sealing element is a detent ball.

7. A resealable cap for a container according to claim 6, wherein said detent ball is positioned against said depression such that the distance between the center point of said detent ball and said depression is greater than the radial distance of said lumen.

8. A sealed sample container which comprises a cuvette for holding a sample solution and a cap covering said cuvette and having a straight hole passing through the cap for insertion of a probe nozzle, the hole having a proximal end and a distal end, the hole being closed by a sealing element positioned within the hole and which blocks fluid flow through the hole when the nozzle is not inserted, said cap comprising a compartment in communication with the hole and positioned for enabling the nozzle to dislodge the sealing element into the compartment from the hole closing position when the nozzle is inserted, wherein the compartment is positioned at an angle greater than zero degrees with respect to the hole and is located between said proximal and distal ends.

9. A sealed sample container according to claim 8, wherein the compartment is in communication with the hole on one end and is a bore through the cap on another end; the cap further comprising a removable stopper disposed in the compartment to retain the sealing element therein.

10. A sealed sample container according to claim 8, wherein the hole includes a recessed area on its inner surface to accept the sealing element in a sealing engagement when the sealing element is in the hole closing position.

11. A sealed sample container according to claim 8, further comprising a spring disposed in the compartment for biasing the sealing element towards the hole closing position.

12. A sealed sample container according to claim 11, wherein the compartment connects to the hole at an acute angle greater than zero degrees such that the direction of movement of the sealing element is partially in the direction of the force of the needle, thereby requiring less force to move the sealing element against the force of the spring.

13. A sealed sample container according to claim 8, wherein the sealing element comprises a detent ball.

14. A sealed sample container according to claim 13, wherein the detent ball is deposed against the recessed area in the hole closing position such that the distance between the center point of the detent ball and the recessed area is greater than the radial distance of the hole.

* * * * *